(12) United States Patent
Jordan et al.

(10) Patent No.: US 8,702,721 B2
(45) Date of Patent: Apr. 22, 2014

(54) INTRALUMINARY STENT RELOCATING APPARATUS

(75) Inventors: Gary A. Jordan, Litchfield, NH (US); Mark D. Wood, Shrewsbury, MA (US)

(73) Assignee: Boston Scientific Schimed, Inc., Maple Grove, MN (US)

( * ) Notice: Subject to any disclaimer, the term of this patent is extended or adjusted under 35 U.S.C. 154(b) by 0 days.

(21) Appl. No.: 13/482,508

(22) Filed: May 29, 2012

(65) Prior Publication Data

US 2012/0232639 A1    Sep. 13, 2012

Related U.S. Application Data

(63) Continuation of application No. 12/107,465, filed on Apr. 22, 2008, now Pat. No. 8,187,284.

(60) Provisional application No. 60/913,420, filed on Apr. 23, 2007.

(51) Int. Cl.
*A61F 11/00*    (2006.01)

(52) U.S. Cl.
USPC ............................................. 606/108

(58) Field of Classification Search
USPC ........ 606/108, 191, 198, 200; 623/1.11, 1.12, 623/1.23
See application file for complete search history.

(56) References Cited

U.S. PATENT DOCUMENTS

| | | | |
|---|---|---|---|
| 4,873,978 A * | 10/1989 | Ginsburg | 606/198 |
| 5,035,706 A | 7/1991 | Gianturco et al. | |
| 5,474,563 A * | 12/1995 | Myler et al. | 606/108 |
| 5,643,282 A | 7/1997 | Kieturakis | |
| 6,106,531 A | 8/2000 | Schatz | |
| 6,258,098 B1 | 7/2001 | Taylor et al. | |
| 6,569,181 B1 | 5/2003 | Burns | |
| 6,652,569 B1 | 11/2003 | Taylor et al. | |
| 2002/0138097 A1* | 9/2002 | Ostrovsky et al. | 606/200 |
| 2004/0147939 A1 | 7/2004 | Rabkin et al. | |
| 2005/0137699 A1* | 6/2005 | Salahieh et al. | 623/2.11 |
| 2006/0276873 A1 | 12/2006 | Sato | |
| 2006/0276887 A1 | 12/2006 | Brady et al. | |

* cited by examiner

*Primary Examiner* — Ryan Severson
*Assistant Examiner* — Jonathan W Miles
(74) *Attorney, Agent, or Firm* — Vidas, Arrett & Steinkraus

(57) ABSTRACT

An apparatus for moving an object disposed within a body lumen. The apparatus includes a first sheath, a coupling member and at least one contraction member for engaging at least a portion of the object. The coupling member is movable relative to the first sheath between a retracted position and a capture position. In the retracted position, a distal portion of the coupling member is disposed within the first sheath. In the capture position, the coupling member distal portion is disposed outside the first sheath. The coupling member is also selectively attachable to the object in at least the capture position. When the coupling member is attached to the object and the contraction member is directly engaged with the object, a predetermined coupling member movement relative to the contraction member radially contracts at least a portion of the object thereby facilitating movement of the object within the body lumen.

13 Claims, 8 Drawing Sheets

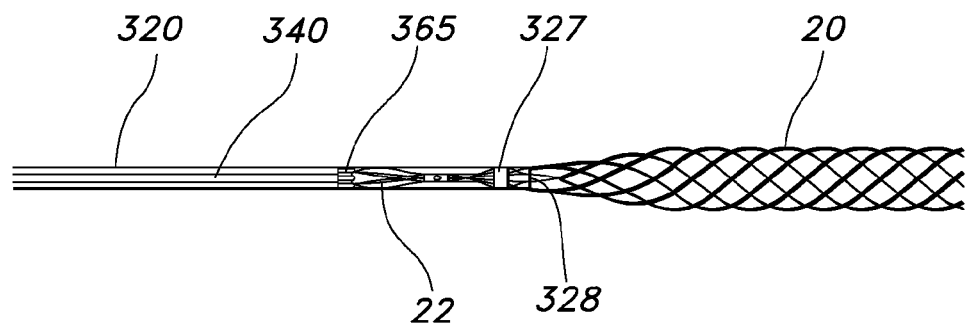
FIG. 14
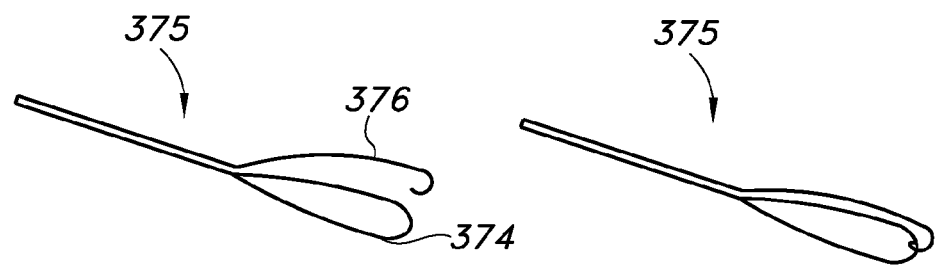
FIG. 15A  FIG. 15B
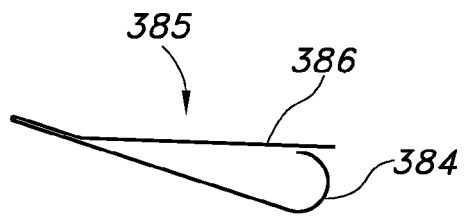
FIG. 16
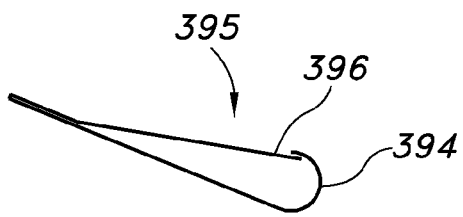
FIG. 17

INTRALUMINARY STENT RELOCATING APPARATUS

CROSS-REFERENCE TO RELATED APPLICATIONS

This application is a continuation application of U.S. application Ser. No. 12/107,465, filed on Apr. 22, 2008, which claims the benefit of U.S. Provisional Patent Application Ser. No. 60/913,420 filed on Apr. 23, 2007, the entire disclosures of which are hereby incorporated herein by reference.

FIELD OF THE INVENTION

This invention relates to a method and system for treatment of body lumens with stents and other prostheses, and more particularly to an apparatus, system and method for retrieving, adjusting and/or repositioning an intraluminal prosthesis, such as a stent, within a body lumen.

BACKGROUND OF THE INVENTION

An intraluminary prosthesis is a medical device used in the treatment of diseased bodily lumens. One type of intraluminary prosthesis used in the repair and/or treatment of diseases in various body lumens is a stent. A stent is generally a longitudinal tubular device formed of biocompatible material, which is useful to open and support various lumens in the body. For example, stents may be used in bodily vessels, such as in the coronary or peripheral vasculature, esophagus, trachea, bronchi colon, biliary tract, urinary tract, prostate, brain, as well as in a variety of other applications in the body. These devices are implanted within the vessel to open and/or reinforce collapsing or partially occluded sections of the lumen. While stents and other intraluminary prosthesis are foreign objects to the human body, they are designed to remain within a body lumen for prolonged periods or even indefinitely.

Stents generally include an open flexible configuration. This configuration allows the stent to be inserted through curved vessels. Furthermore, this configuration allows the stent to be configured in a radially compressed state for intraluminary catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminary vascular stents, have included helically wound coils which may have undulations or zigzags therein, slotted stents, ring stents, braided stents and open mesh wire/filament stents, to name a few. Super-elastic materials and metallic shape memory materials have also been used to form stents.

On occasion there is a need to retrieve or reposition a stent previously deployed in a body lumen. For example, a stent may require repositioning if incorrectly located during deployment, or if it migrates after deployment. Also, the need to retrieve or remove a deployed stent may arise from a post-deployment determination that the stent was not the appropriate size for the application, or from a procedure that calls for only temporary use of the stent.

One known approach to removing a previously deployed stent or other prosthesis involves capturing a proximal end of the object with biopsy forceps or other snare, then pulling proximally to withdraw the object. One problem with this approach is that pulling or pushing a fully radially expanded stent through a body lumen can damage surrounding tissue and the stent itself.

Therefore, there is a need for a reliable and effective apparatus, system and method for removing, adjusting and/or repositioning an intraluminary prosthesis that has already been deployed, which overcomes the shortcomings set forth above while also having application to other select intraluminary objects.

SUMMARY OF THE INVENTION

The present invention is directed to an apparatus, system and method for moving an object disposed within a body lumen. In particular, the present invention relates to an apparatus and method for using the apparatus for retrieving, adjusting and/or repositioning an intraluminary prosthesis, such as a stent.

In one embodiment of the present invention an apparatus for moving an object disposed within a body lumen includes a first sheath for insertion into the body lumen, a coupling member and at least one contraction member for engaging at least a portion of the object. The coupling member is movable relative to the first sheath between a retracted position and a capture position. In the retracted position, a distal portion of the coupling member is disposed within the first sheath. In the capture position, the coupling member distal portion is disposed outside the first sheath. The coupling member is also selectively attachable to the object in at least the capture position. When the coupling member is attached to the object and the contraction member is directly engaged with the object, a predetermined coupling member movement relative to the contraction member radially contracts at least a portion of the object thereby facilitating movement of the object within the body lumen.

Additionally, the coupling member and the contraction member of the apparatus can cooperate to draw the object at least partially within the first sheath. Also, the coupling member can include at least one first grasping member for removeably attaching to the object, wherein the first grasping member includes at least one of a hook, forceps, clamp and snare. The contraction member can include a deployable funnel with an inner passage for receiving the object, with at least one portion of the funnel being selectively adjustable between a radially compressed and a radially expanded configuration. Further, another predetermined coupling member movement relative to the funnel can encourage the funnel to adjust to the expanded configuration. Also, the coupling member can be axially moveable relative to the funnel and the funnel can be axially moveable relative to the first sheath. Further, at least a distal portion of the coupling member can be disposed within the inner passage when the coupling member is in the retracted position. Further still, the coupling member can include at least one stop member for limiting axial movement of the coupling member relative to the funnel. Yet further still, the coupling member can include a cap, whereby the cap retains the funnel in the compressed configuration. Yet further still, the funnel can be disposed at a distal end of the first sheath and/or integrally formed with the first sheath.

Also, the contraction member can include a second sheath moveably disposed with respect to the first sheath, wherein at least a portion of the second sheath is coaxially disposed within the first sheath. The coupling member can further include at least one elongate rod extending generally parallel to the first sheath. The first grasping member can be disposed on a distal end of the rod. Also at least a portion of the rod can be biased to diverge radially away from a central longitudinal axis of the sheath. Additionally, at least one elongate rod can extend from a distal end of the second sheath. The rod can extend generally parallel to at least one of the first and second sheath, wherein at least a distal portion of the rod can be disposed outside the first sheath when the contraction member is in the capture position. Further the contraction member can include at least one second grasping member for removeably attaching to the object, whereby the first and second grasping members can cooperate to radially contract the object. Additionally, when in the capture position the first grasping member can secure to a distal portion of the object and the second grasping member can secure to a proximal portion of the object.

In another embodiment of the present invention a method for moving an intraluminary object disposed within a body includes providing a first sheath for insertion into a body lumen, a coupling member and at least one contraction member for engaging at least a portion of the object. The coupling member is movable relative to the first sheath between a retracted position wherein a distal portion of the coupling member is disposed within the first sheath and a capture position wherein the coupling member distal portion is disposed outside the first sheath. The coupling member is selectively attachable to the object in at least the capture position. Also, when the coupling member is attached to the object, a predetermined coupling member movement relative to the contraction member radially contracts at least a portion of the object thereby facilitating movement of the object within the body lumen.

Additionally, the method can further include inserting the first sheath, the coupling member and the contraction member into the body lumen with at least the coupling member in a retracted position. Also, the method can further include moving the coupling member into the capture position and attaching the coupling member to the object. Further, the predetermined coupling member movement can be initiated in order to move the object relative to the body lumen. Also, the coupling member and the contraction member of the method can cooperate to draw the object at least partially within the first sheath. Further, the coupling member of the method can includes at least one grasping member for removeably attaching to the object. The grasping member can include at least one of a hook, forceps, clamp and snare. Also, the coupling member can include at least one elongate rod extending generally parallel to the first sheath. The grasping member of the method can be disposed on a distal end of the rod. Also, the predetermined coupling member movement can include a distal portion of the coupling member moving at least one of toward and away from a distal portion of the contraction member. Further, the radial contraction of the object can be associated with at least one of an elongation of the object and extrusion of the object through the contraction member.

These and other objectives, features, and advantages of this invention will become apparent from the following detailed description of illustrative embodiments thereof, which is to be read in connection with the accompanying drawings.

BRIEF DESCRIPTION OF THE DRAWINGS

FIGS. 12-14 illustrate sequential perspective views of the apparatus of FIGS. 10 and 11 actuated to radially contract the intraluminal prosthesis.

FIGS. 15a and 15b illustrate an alternative embodiment of the grasping members in accordance with the subject invention.

FIGS. 16 and 17 illustrate further alternative embodiments of the grasping members in accordance with the subject invention.

DETAILED DESCRIPTION OF THE INVENTION

The present invention relates to an apparatus, system and method for moving an object disposed in a bodily passageway. The invention allows the clinician or operator to remove or adjust the position of the object while minimizing damage to the object itself and the surrounding tissue. The assembly is preferably suited for medical applications (particularly, endoscopic therapy) in the gastrointestinal tract, the biliary tract, the urinary tract, and the respiratory tract. In particular, a preferred embodiment of the present invention is directed to an assembly, system and method for retrieving, adjusting and/or repositioning an intraluminary prosthesis, such as a stent in a biliary duct. Additionally, an assembly in accordance with the present invention could be used in the neurological system (e.g., in the brain) and in the cardiovascular system (e.g., in the heart). Reference herein to bodily passageways or lumens may be to vessels or passageways in any of the aforementioned tracts and systems or elsewhere in the body. While discussed below primarily in connection with retrieving radially self-expanding stents, the apparatus and systems of the present invention can also be used to recover or reposition other types of stents and prostheses (e.g., stent-grafts). Additionally, in accordance with the present invention the assembly could also be used to remove other objects from within a body lumen.

It should be noted that references herein to the term "distal" are to a direction away from an operator of the subject invention, while references to the term "proximal" are to a direction towards the operator of the subject invention. Accordingly, when the terms "distal" and "proximal" are used herein in the context of an assembly device that is being deployed within a body, such as a human body, by an operator, the term "distal"

refers to a location within the body that is further within the body than a location that is "proximal" to the operator.

Figure 1:
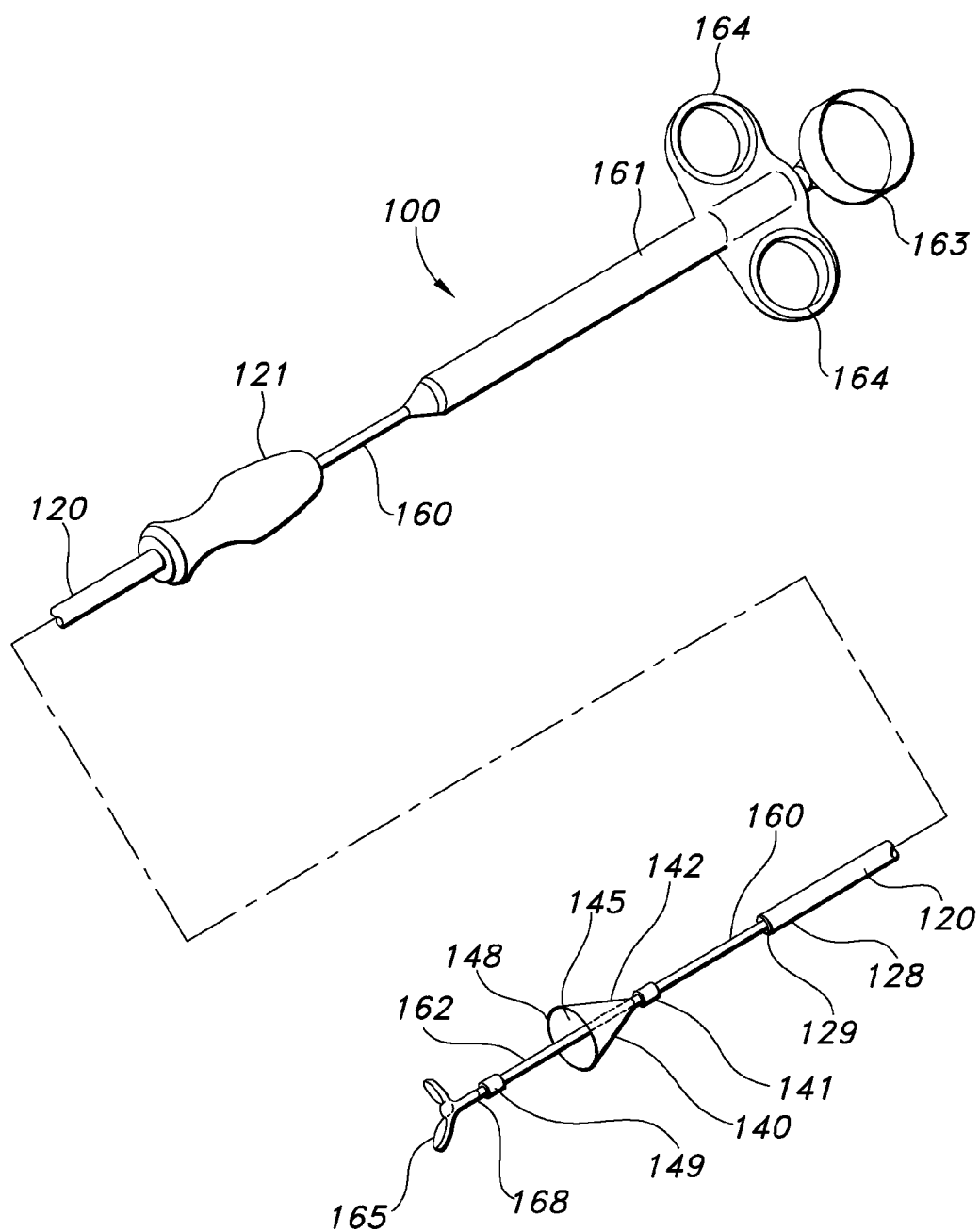
FIG. 1 illustrates a perspective view of an embodiment of the apparatus for moving an intraluminal prosthesis in accordance with the subject invention.

With reference to the drawings, FIG. 1 shows an apparatus 100 for moving an object, such as a stent, disposed within a passageway or body lumen. The apparatus 100 is preferably used for retrieving, adjusting and/or repositioning a radially contractible stent or other prosthesis previously deployed in a body lumen. Apparatus 100 includes a sheath member 120, at least one contraction member 140 and a coupling member 160. In FIG. 1, the apparatus 100 is shown in an extended or deployed position. However, contraction member 140 and coupling member 160 can preferably be retracted so they are substantially disposed inside sheath 120. In this way, the retracted configuration of apparatus 100 can have the narrower profile of sheath 120 and can be more easily inserted into and navigated within a body lumen. Once positioned in a desired location/configuration within a body lumen, contraction member 140 and coupling member 160 can be axially deployed from inside sheath 120. It should be noted that the apparatus 100, or portions thereof, can be used as part of or in conjunction with other endoscopic systems.

FIGS. 2-5 illustrate the apparatus 100 inserted in a body lumen 10 in various stages of deploying and attaching to stent 20. The elongate pliable sheath 120 preferably has a handle 121 at its proximal end to facilitate manipulation of the sheath. At its distal end 128 the sheath 120 includes an aperture 129 for deploying the inner elements. Sheath 120 is preferably designed for entry into the body, and transluminal travel to a selected site in a body lumen 10. To this end, the sheath is pliable in the sense that it readily bends to accommodate curved or serpentine luminal passages, yet has sufficient axial stiffness to allow control of the transluminal travel from the proximal end of the sheath. A sheath lumen 125 runs longitudinally through the sheath 120.

Sheath 120 is preferably formed of a body compatible material. Desirably, the biocompatible material is a biocompatible polymer. Examples of suitable biocompatible polymers include, but are not limited to, polypropylene (PP), polytetrafluoroethylene (PTFE), polyethylene terephthalate (PET), high density polyethylene (HDPE) and the like. Additionally, the sheath 120 could have layers, coverings, films, coatings, and the like, desirably a polymeric covering, disposed over the outer or inner surfaces to improve interaction with the body lumen and the inner elements discussed below. Further, the sheath 120 or select portions thereof could be clear, opaque, translucent, colored and/or non-transparent as desired.

FIGS. 1-5 also illustrate an embodiment of the contraction member 140 in accordance with the present invention. Preferably, contraction member 140 forms a distally diverging or expanding cone or funnel. The funnel 140 is preferably formed of an elastic material that can be compressed to fit inside sheath 120 and will expand once no longer radially constricted. In this way, it can be axially moved beyond the distal end 128 of sheath 120, thus allowing at least a distal portion 148 of the funnel 140 to expand and diverge from the narrower collar portion 142, forming a funnel-shaped element. An inner passage 145 of the funnel 140 is adapted to receive at least a portion of the select object disposed within a body lumen intended for movement.

The funnel 140 is preferably formed of a material or materials can radially expand and provide sufficient stiffness to act as a funneling member for a prosthesis pulled through its inner passage 145. The funnel 140 can be formed of materials similar to those used for contemporary self-expanding stents. Thus, the funnel 140 can be formed of metals, plastics or other materials, however it is preferred that a biocompatible construction is employed. Useful biocompatible materials include but are not limited to biocompatible metals, biocompatible alloys, biocompatible polymeric materials, including synthetic biocompatible polymeric materials and bioabsorbable or biodegradable polymeric materials, materials made from or derived from natural sources and combinations thereof. Useful biocompatible metals or alloys include, but not limited to, nitinol, stainless steel, cobalt-based alloy such as Elgiloy, platinum, gold, titanium, tantalum, niobium, polymeric materials and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonlimiting examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Further, the funnel 140 may include materials made from or derived from natural sources, such as, but not limited to collagen, elastin, glycosaminoglycan, fibronectin and laminin, keratin, alginate, combinations thereof and the like.

Also, it should be understood that the materials of the funnel 140 as well as the component filaments of the funnel 140 can be further enhanced with coverings, films, coatings, and other materials and techniques. A covering may be composed of polymeric material and/or silicone. The covering may also comprise any plastic or polymeric material, desirably a somewhat hard but flexible plastic or polymeric material. The covering may be transparent or translucent, desirably substantially or partially transparent. Furthermore, the covering may be constructed of any suitable biocompatible materials, such as, but not limited to, polymers and polymeric materials, including fillers such as metals, carbon fibers, glass fibers or ceramics. Useful covering materials include, but are not limited, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. The coating or coatings may be on the entire funnel 140 or portions thereof.

Preferably, the funnel 140 includes a narrowed collar portion 142 on its proximal end providing a sliding mounted engagement with control rod 162. The collar portion 142 is preferably banded or permanently restricted in some way from radial expansion. The collar portion 142 should be suitably sized to allow relative axial movement between funnel 140 and control rod 162. However, such axial movement is preferably limited to movement between two spaced apart stop members 141, 149. Thus, the inner diameter of the collar portion 142 should not exceed the outer diameter of stop members 141, 149 in order to ensure the appropriate limited relative axial movement. Also, funnel 140 and control rod 162 are both preferably axial moveable relative to sheath 120.

The stop members 141, 149 are preferably secured to rod 162 for limiting relative movement between the rod 162 and the funnel 140. While stop members 141, 149 are illustrated as radial bands or sleeves secured to rod 162, they could alternatively comprise a small radial protrusion on a portion of rod 162, sufficient to limit funnel collar 142 axial movement. In a further alternative embodiment, the stop members 141, 149 can be the end walls of a longitudinal channel formed in rod 162, with funnel 140 including a pin designed for guided movement within that channel.

The coupling member 160 includes an elongate pliable tube or control rod 162, a rod handle 161 and at least one capture or grasping member 165 for attaching to a stent or other object. The coupling member 160 is coaxially disposed with and axially moveable relative to the sheath 120. However, it should be understood that locking elements (not shown) could be provided to adjustably fix the relative position of the sheath 120 and coupling member 160 as desired. Also, preferably located at the distal end 168 of control rod 162 is the grasping member 165. The control rod 162 is also preferably made of one of the biocompatible materials mentioned above with regard to the sheath 120. However, the control rod 162 could be made of the same or a different material as the sheath 120.

Grasping member 165 is used to grab or attach itself to an intraluminary prosthesis, such as a stent. Preferably, grasping member 165 is formed like forceps with a pair of clamping surfaces or jaws (with or without serrations) mounted to pivot relative to the control rod 162 about a transverse axis. It should be understood, however, that grasping member 165 could alternatively be formed as a hook or snare as illustrated in the later embodiments discussed below. The jaw pivoting style grasping member 165 is preferably controlled through one or more wires, sutures or filaments (not shown). The wires are coupled to grasping member 165 and extend through one or more lumens in the control rod 162 to a control handle 161 disposed at or near the proximal end of the control rod 162.

The rod handle 161 is preferably provided with manipulating features 163, 164 for controlling the position, configuration and orientation of the grasping member 165. Also, preferably the proximal manipulating feature 163 is moveable relative to the adjacent manipulating feature 164 in order to open and close grasping member 165 as desired. Feature 163 can be pulled axially away from feature 164 in order to open grasping member 165. Alternatively, the relative movement between features 163, 164 could be rotational or some other movement which would actuate grasping member 165. Also, preferably feature 163 is axially biased through a spring-type mechanism (not shown), encouraging it to return to a position which closes grasping member 165. Such a spring-type mechanism could be located in the rod handle 161.

Figure 2:
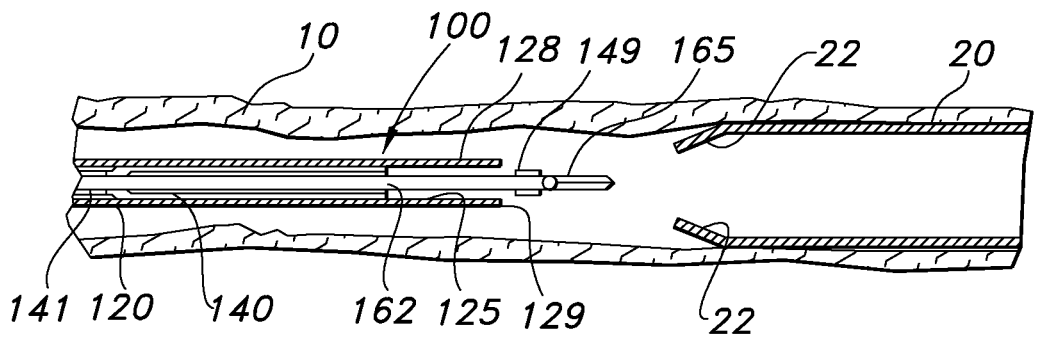
FIG. 2 illustrates a plan view of a distal portion of the apparatus of FIG. 1 in cross-section disposed within a body lumen adjacent an intraluminal prosthesis.

FIGS. 2-5 illustrate the use of apparatus 100 to retrieve, adjust and/or reposition an intraluminally deployed stent 20. When initially advanced to the site of a deployed stent 20, the apparatus 100 is preferably fully or at least substantially retracted, with the funnel 140 fully contained within sheath 120. Once the surgeon or operator is prepared to engage the target object, the rod handle 161 can be moved in the distal direction, while holding the sheath handle 121 stationary, toward a capture position as illustrated in FIG. 2. Alternatively, the surgeon could move the sheath handle 121 proximally, while holding the rod handle 161 stationary. Either way, the result of this relative axial movement between members is that the sheath 120 is retracted from covering at least the grasping member 165. The operator could find advantage in deploying the grasping member 165, and not the funnel 140, in order to more freely position the device 165 and attach it to the target object 20. This prevents the funnel 140 from interfering with the effort to guide and/or position the grasping member 165.

Figure 3:
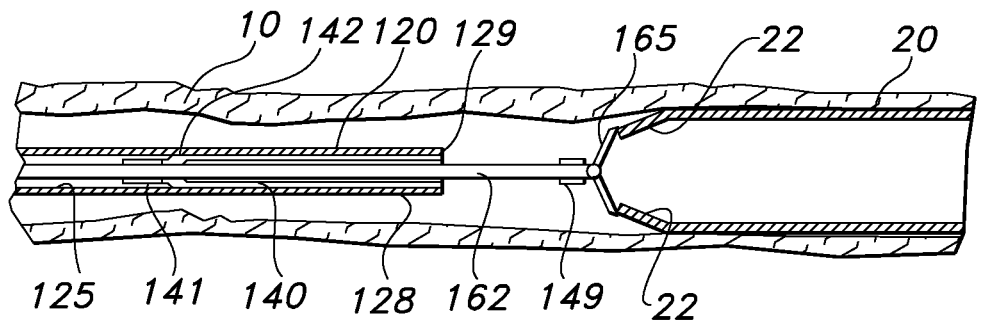
FIGS. 3-5 illustrate sequential plan views in cross-section of the apparatus of FIGS. 1 and 2 moving to capture and move the intraluminal prosthesis.
Figure 4:
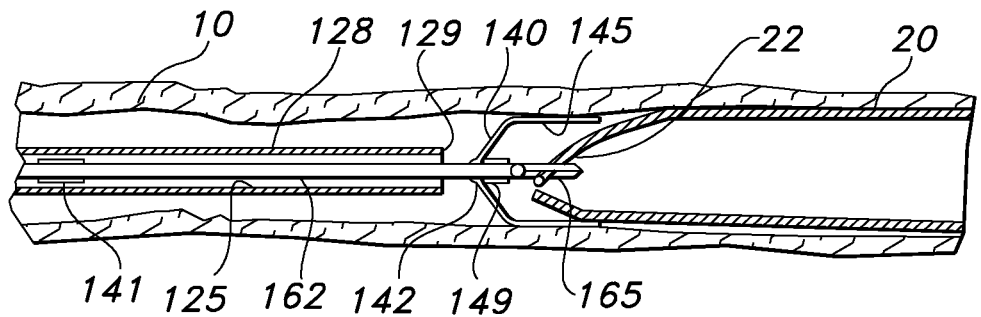
Figure 11:
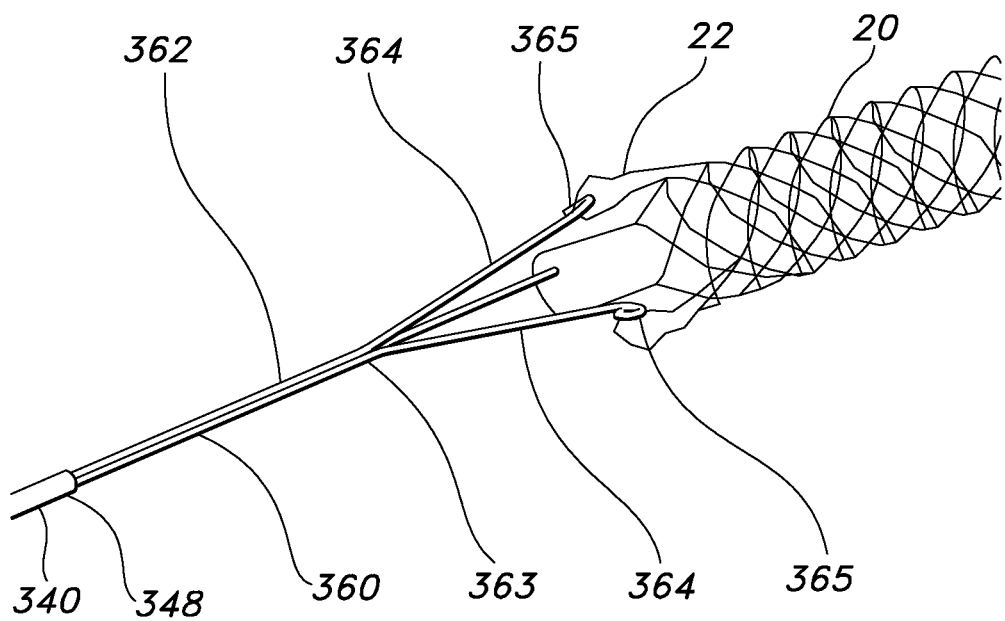
FIG. 11 illustrates a perspective view of the apparatus of FIG. 10 removeably attached to an intraluminal prosthesis.

With the jaws of the grasping member 165 properly aligned with the target object, the operator can then manipulate the grasping member 165 to engage a portion thereof. Pulling manipulating feature 163 proximally, while maintaining sheath handle 121 and rod handle 161 in place, causes the clamping surfaces to open, as illustrated in FIG. 3. Then by pushing or, if biased, allowing manipulating feature 163 to return to its more distal closed position the user can grasp or capture a portion of the target object, as illustrated in FIG. 4. This task can be made easier when the target object is a stent 20 that includes end portions 22 that are not quite as fully radially expanded as the rest of the stent. For example, many contemporary stents 20 include end loops (as illustrated in FIG. 11) that, even in there fully deployed configuration, tend to deflect radially inwardly slightly. Thus, an operator might have an easier time snagging one of these end loops or a similar deflecting end portions 22 with the grasping member 165.

Figure 5:
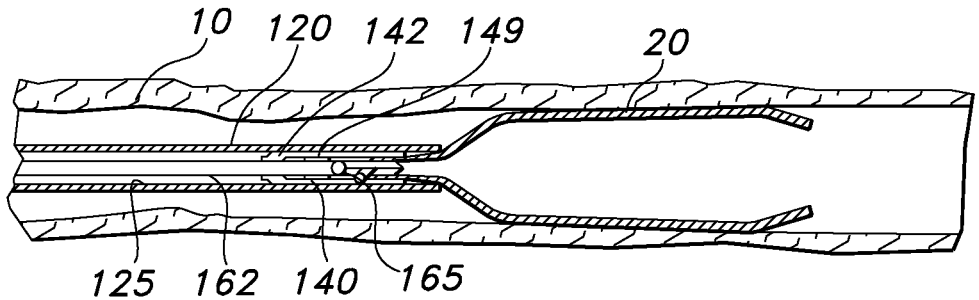

Once the grasping member 165 is attached to the stent 20, the operator preferably moves sheath handle 121 toward the rod handle 161 to further retract sheath 120 until funnel 140 is deployed and expands to the open configuration, as illustrated in FIG. 4. Although funnel 140 is slidingly mounted on control rod 162, stop member 141 will engage and push on the collar portion 142 of funnel 140, causing the funnel 140 to deploy. Thereafter, the stent 20 can be pulled toward the sheath 120, by holding sheath handle 121 in place and moving rod handle 161 proximally. It should be noted that due to a relatively low-friction mounting of funnel collar 142 about the control rod 162, funnel 140 will generally not immediately enter the distal aperture 128 of sheath 120. During at least the initial retraction of grasping member 165 and control rod 162, the funnel 140 will tend to slide along rod 162 until collar 142 abuts stop member 149, as illustrated in FIG. 4. Once stop member 149 engages funnel collar 142, the funnel 140 can be pulled back into sheath 120. Additionally, it should be noted that once stop member 149 and funnel collar 142 are engaged, the grasping member 165, along with at least the attached portion of the stent 20, should be disposed within the inner funnel passage 145. Thereafter, further pulling the rod handle 161 proximally away from sheath handle 121 draws funnel 140, grasping member 165 and at least the attached portion of the stent 20 into the outer sheath 120 as illustrated in FIG. 5.

Preferably, during the final phases of retraction the funnel 140 radially compresses a proximal portion of stent 20 and guides it into the sheath 120. As the funnel 140 is drawn back into the sheath 120, it is radially compressed by the sheath 120 and in turn radially compresses at least a proximal portion of the stent 20. Once at least a proximal portion of the stent 20 is drawn into the sheath 120, it can more easily be moved proximally within the body lumen 10. The stent 20 could also be fully drawn into sheath 120 for complete removal from the body lumen 10. Also, even if the stent 20 is not easily radially compressible, if at least the edge portion 22 can be drawn into funnel channel 145, the preferably low-friction outer surface of funnel 140 can more gently guide the leading edge of the stent 20 as it is being pulled through the body lumen 10.

Further, if stent 20 is a self-expanding stent, distal repositioning can be achieved by retracting the entire stent 20 into sheath 120. Once the stent 20 is loaded in apparatus 100, the loaded assembly can be moved distally to the target repositioning location. Then the sheath 120 can be retracted and grasping member 165 opened, thereby releasing and redeploying the stent 20.

FIGS. 6-9 illustrate an alternative embodiment of the apparatus of the present invention. The distal end of an apparatus 200 is shown, along with a stent 20. The apparatus 200 includes a sheath member 220, at least one contraction member 240 and a coupling member 260. It should be understood that although the proximal end of this and some later embodiments is not shown, they can have the same or similar designs to those illustrated in FIG. 1 or 18, or other similar assemblies known in the field of endoscopy.

Apparatus 200 preferably includes an elongate pliable sheath 220 having the same or similar construction and/or composition as that of sheath 120 described above. A lumen 225 preferably extends axially along the length of sheath 220. Additionally, a distal end region 224 of sheath 220 is designed to radially expand or flare when unrestrained or otherwise actuated to do so.

Figure 7:
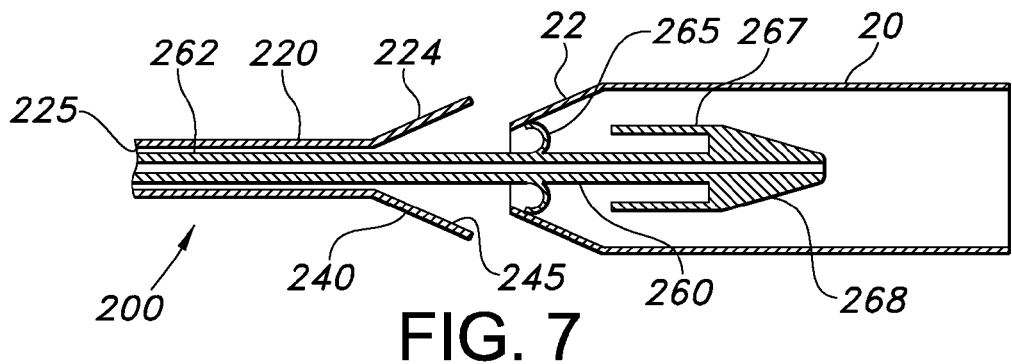
FIGS. 7-9 illustrate sequential plan views in cross-section of the apparatus of FIG. 6 moving to capture and move the intraluminal prosthesis.
Figure 8:
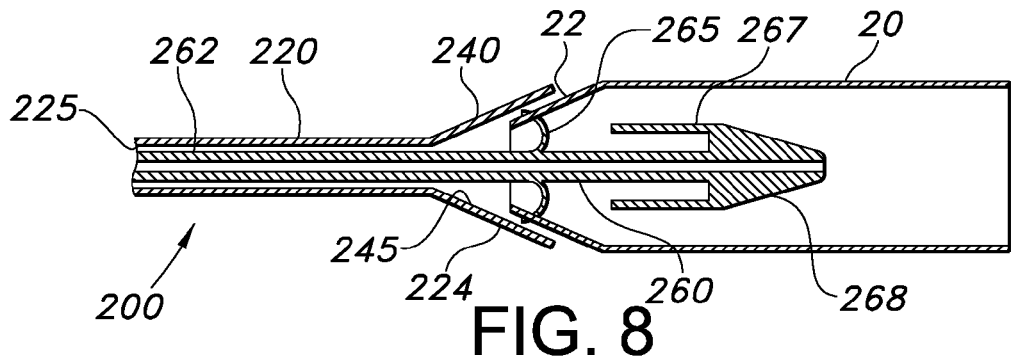
Figure 9:
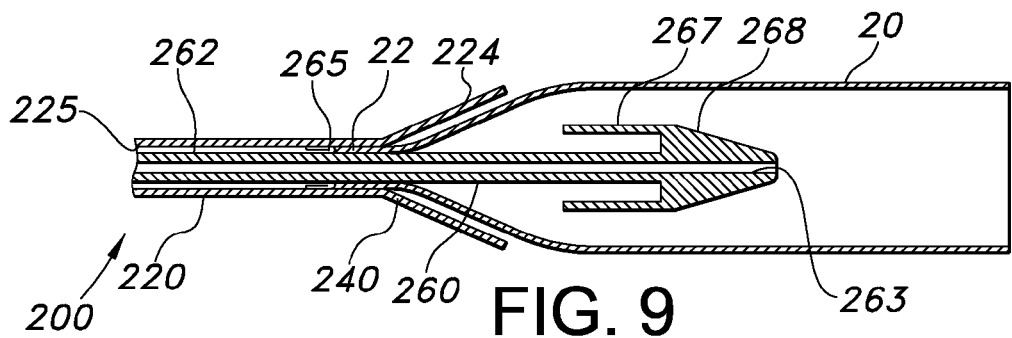

As illustrated in FIGS. 7-9, the radially expanded end region 224 forms a contraction member or funnel 240. Thus, funnel 240 includes a conical inner passage 245 intended for receiving a targeted intraluminary object. Although end region 224 is illustrated as being formed of the same material as the rest of sheath 220, it could be formed from a more flexible self-expanding material, such as those described for funnel 140 above. Nonetheless, funnel 240 is preferably either integrally formed with or fixedly secured to the rest of sheath 220.

Figure 6:
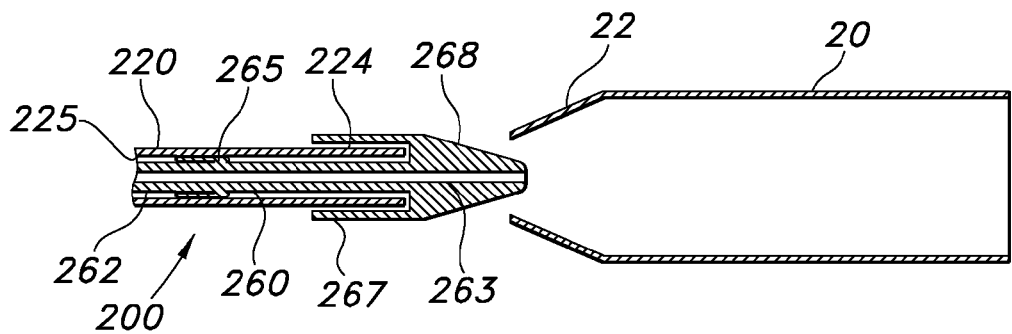
FIG. 6 illustrates a plan view of a distal portion in cross-section of an alternative embodiment of the apparatus in accordance with the subject invention adjacent an intraluminal prosthesis.

Coupling member 260 includes an elongate pliable control rod 262, which preferably extends coaxially with sheath 220. Control rod 262 is axially moveable relative to the sheath 220, similar to the relationship between rod 162 and sheath 120 discussed above. Preferably, coupling member 260 includes an inner lumen 263, which extends therethrough. Lumen 263 can be used as a flush port, guide wire channel or other suitable access to a desired bodily passageway. The distal end of rod 262 includes a head 268 that preferably narrows and converges in the distal direction. As illustrated in FIG. 6, the head 268 acts as the leading distal edge for the overall apparatus 200 when it is being inserted into body cavities and lumens. Thus, the converging head 268 can assist in navigating through narrow passageways within the body. The head 268 can be formed of the same material as the rod 262, as illustrated, or it could be formed from another material. In fact, head 268 could be formed to provide a more or less rigid composition than that of flexible rod 262. However, it is preferable that head 268 be either integrally formed with or fixedly secured to rod 262.

Additionally, a proximal portion of the head 268 is preferably formed as a proximally protruding sleeve or annular flange 267. As illustrated in FIG. 6, the flange 267 is sized to fit over, in concentric fashion, and restrain end region 224 from radially expanding. However, once coupling member is moved distally relative to the sheath 220 and flange 267 is no longer engaged with end region 224, radial expansion occurs and funnel 240 is thus deployed.

Coupling member 260 also includes grasping member 265. Preferably, grasping member 265 includes one or more radially protruding hooks, barbs or snares designed to catch and hold an end portion 22 of stent 20. The grasping member 265 is preferably self-expanding, so it can be deployed from a radially compressed state when contained within sheath lumen 225 to a radially expanded state as illustrated in FIGS. 7 and 8.

FIGS. 6-9 together illustrate a sequence for using apparatus 200 to retrieve a previously deployed stent 20. Initially, apparatus 200 is intraluminally inserted and advanced to the region immediately adjacent to where the stent 20 is located, as illustrated in FIG. 6. As shown, during that initial insertion stage, control member 260 is preferably maintained in a proximal or retracted position with respect to sheath 220. Then, while holding the sheath 220 relatively still, the control member 260 is advanced distally until the grasping members 265 are surrounded by at least the proximal end portions 22 of the stent 20, as illustrated in FIG. 7. At this point, both the funnel 240 and grasping members 265 are preferably deployed as shown. Thereafter, the control member 260 is retracted in order to engage and snare or attach one or more of the grasping members 265 with the stent 20, as illustrated in FIG. 8. Then by holding sheath 220 steady and pulling control member 260 further in the proximal direction relative to the sheath 220, at least the proximal portions of the stent 20 are made to radially contract as they are pulled into the funnel 240, as illustrated in FIG. 9. In this last configuration, with at least the proximal end 22 of stent 20 constricted, it can more easily be pulled proximally through the body lumen. As mentioned with regard to the earlier embodiments, apparatus 200, or portions thereof, can be used as part of or in conjunction with other endoscopic systems.

Alternatively, the grasping members 265, in the form of self-expanding radially extending hooks or snares, need not extend from the rod 262. In this alternative, embodiment the flange 267 proximally extending from the head 268 of the coupling member 260 is used to catch the stent 20. By pulling the head 268 proximally and trapping or pinching an end portion of the stent 22 between the proximal edge of the flange 267 and the inner surface 245 of the funnel 240, the apparatus 200 can be alternatively used to move an intraluminary object. Thus, the proximal edge of the flange 267 can also act as a grasping member. Also, rather than flange 267 being formed as an annular sleeve, it can be formed as several elongate fingers or tabs axially extending from the proximal peripheral edge of head 268. Such tabs can then either clamp a portion of the stent 22 or snare an end loop of the stent 20, hooking and trapping it between the tabs and the funnel 240.

In yet a further alternative embodiment of apparatus 200, a relatively smaller head 268 is provided than that shown in FIG. 6-9. In this embodiment, preferably the smaller version of head 268 fits within sheath lumen 225, whereby the head 268 and the full length of the stent are retracted into all or a portion of the sheath 220.

Figure 10:
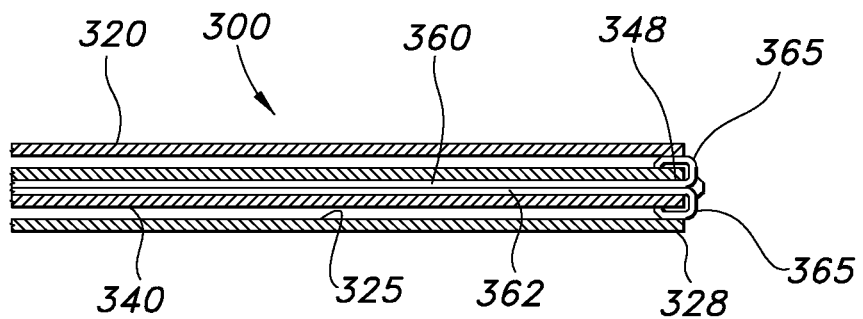
FIG. 10 illustrates a plan view in cross-section of a distal portion of another alternative embodiment of the apparatus in accordance with the subject invention.

FIGS. 10-14 illustrate a further alternative embodiment of the apparatus of the present invention. In particular, the distal end region of apparatus 300 is shown. Apparatus 300 includes a sheath member 320, at least one contraction member 340 and a coupling member 360. The sheath 320, contraction member 340 and coupling member 360 are all concentrically configured as shown and axially moveable relative to one another. In FIG. 10, the apparatus 300 is shown in a retracted and radially compressed configuration. However, by moving contraction member 340 and coupling member 360 distally (toward the right as illustrated in FIG. 10) relative to sheath 320, the distal portions of the inner members can be extended beyond the distal end of the sheath 320 and thus outside sheath lumen 325. Similarly, by moving coupling member 360 distally relative to the contraction member 340, coupling member 360 will extend beyond the distal end of contraction member 340 and thereby radially expand, as described further below.

Contraction member 340 is preferably formed like the outer sheath 320 in that it is an elongate flexible tube. However, while contraction member 340 and sheath 320 can be formed of the same or similar materials and/or finishes, they can be different if desired. In contrast, coupling member 360 is formed from one or more elongate wires 362 that extend through an inner lumen of contraction member 340. The wires 362 are preferably formed of body compatible materials, such as stainless steel, nitinol, ceramic or polymer based materials. Also, as with the first embodiment, the sheath 320, contraction member 340 and coupling member 360 are each preferably coupled to handles (not shown) that control independent movement of each member relative to the others.

As illustrated in FIG. 11, preferably coupling member 360 is formed by three wires 362 that are fused together over most of the length of the coupling member 360. Respective distal end segments 364 of the wires 362 include a bend 363 which causes the end segments 364 to diverge distally when not constrained. Thus, the distal end segments 364 of the wires 362 are preferably formed with enough elasticity such that the bend 363 can be generally straightened or the diverging segments 364 radially compressed together when held within the contraction member 340, yet self-expanding when deployed therefrom. Additionally, each of the wires 362 respectively supports a grasping member 365 at their distal end.

FIGS. 11-14 also illustrate the apparatus 300 engaged with a stent 20. Preferably, the number of wires 362 and corresponding grasping members 365 included in the apparatus 300 are chosen and configured to correspond to attachable end segments of the stent 20. In this and the other embodiments, it is desirable that stent 20 be formed with an open weave or mesh construction; including multiple helically wound filaments of a flexible body compatible material, examples of which were recited above. The end portions 22 of the stent 20, or at least the proximal end, include(s) loops which can provide a convenient segment for engagement by the grasping members discussed herein. Alternatively, the end portions 22 can have a smaller loops or bends. Such bends or loops can be formed by a pair of helical windings, the ends of which are curved and either integrally formed or joined together. Such loops or bends provide a convenient coupling point as described herein. Also, such loops or bends are preferably designed to slightly deflect radially inwardly when fully deployed to facilitate engagement by a grasping member as described herein. Accordingly, although a stent 20 when deployed tends to press radially outwardly against surrounding tissue and to a certain extent becomes embedded in that tissue, one or both end portions 22 preferably deflect inwardly, remaining exposed and are readily accessible to the grasping members in accordance with the invention.

FIGS. 11-14 together illustrate a sequence for using apparatus 300 to engage and move a previously deployed stent 20. As with the previous embodiments the apparatus 300 is transluminally advanced in a retracted position to a site in a body lumen near to where the stent 20 has been deployed. Thereafter, the contraction member 340 and control member 360 are advanced further distally, while holding the sheath 320 relatively stationary. In fact, preferably contraction member 340 and control member 360 are advanced together to a point, such that grasping members are axially surrounded by the stent 20, but held in a radially compressed configuration. Then the contraction member 340 is pulled back proximally so that the end segments 364 of the control member 360 are allowed to radially expand and diverge from one another. By delicately proximally pulling the apparatus 300, or at least the control member 360, the grasping members 365 preferably snare and/or trap one or more end portions 22 of the stent 20, as illustrated in FIG. 11. Just prior to this capture phase, the operator may be required to axially rotate portions of the apparatus 300, namely control member 360, in order to align the grasping members 365 with one or more end loops 22 of the stent 20, as shown.

Figure 12:
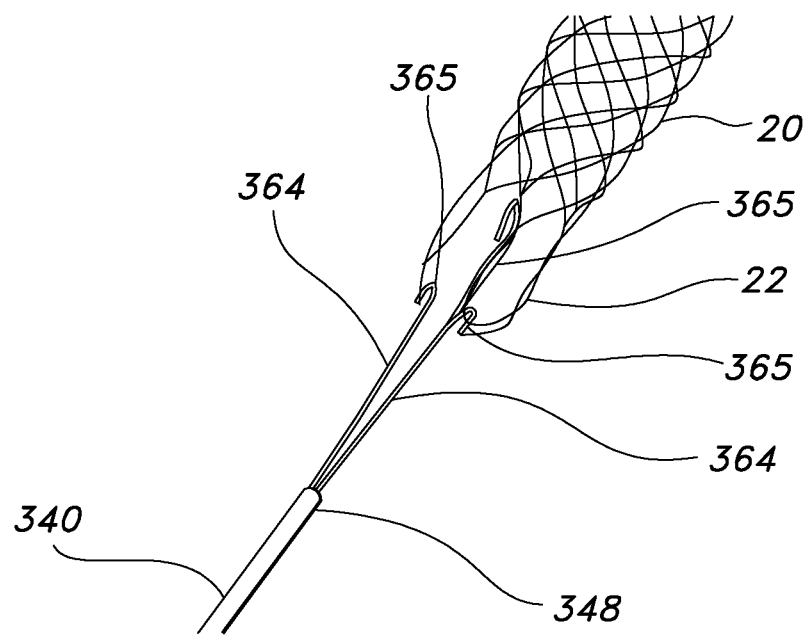

With the coupling maintained between the stent 20 and the grasping member 365, the distal end 348 of contraction member 340 is advanced distally relative to the control member 360, which causes grasping members 365 to radially contract as the end segments 364 enter the lumen of contraction member 340. Alternatively, either the control member 360 can be pulled proximally while holding the contraction member 340 relatively still or both members 340, 360 can be moved to achieve the desired radial inward movement of the grasping members 365. As grasping members 365 are drawn together the end portions 22 of the stent 20 are also radially constricted, as illustrated in FIGS. 12 and 13.

Figure 13:
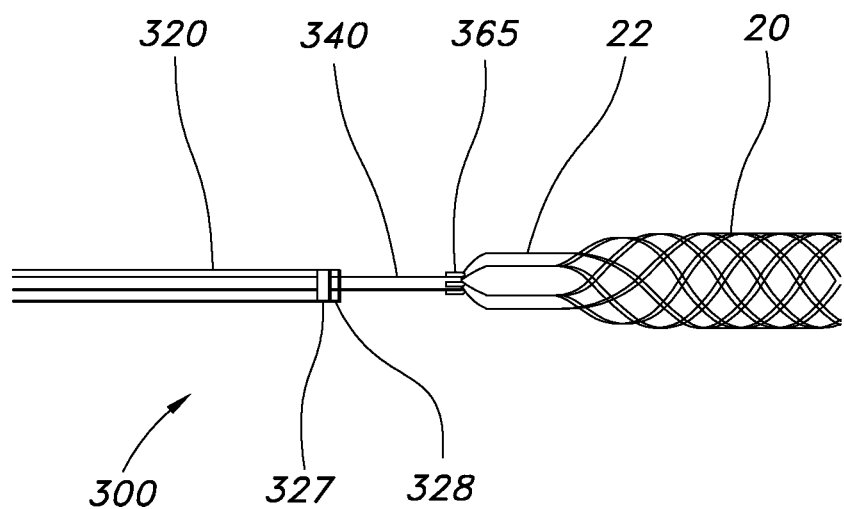

As illustrated in FIG. 13, as the end segments 364 are pulled inside contraction member 340, the grasping members are eventually drawn close to one another along with the stent ends 22. At this stage, the apparatus 300 or portions thereof can be pulled proximally to reposition the stent 20. Thus, grasping members 365 are preferably configured to releasably engage the stent 20 for release while still within the body lumen. Alternatively, as illustrated in FIG. 14, the grasping members 365 can be further drawn into the sheath 320, after which stent 20 repositioning can be accomplished. It should be noted that as with previous embodiments, such repositioning could include removal of the stent 20 from the body lumen or a repositioning and/or reconfiguration of the stent within the body lumen. Also, the entire stent 20 could potentially be drawn inside sheath 320. Additionally, a fully or significantly radially constricted self-expanding stent 20 could also potentially be distally repositioned using these techniques. Further, as mentioned with regard to the earlier embodiments, apparatus 300, or portions thereof, can be used as part of or in conjunction with other endoscopic systems.

FIGS. 13 and 14 further illustrate the use of a radiopaque marker 327, preferably disposed at or near the distal end 328 of sheath 320. Marker 327 can assist the operator in visualizing the relative position of the apparatus 300 with relation to the target object. Such a marker 327 can be formed from radiopaque materials, such as metallic-based powders or ceramic-based powders, particulates or pastes which may be incorporated into the distal sheath 328 material. For example, the radiopaque material may be blended with the polymer composition from which the polymeric filament is formed, and subsequently fashioned into a portion of the sheath 320. Alternatively, the radiopaque material may be applied to the surface of the sheath 320. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated by reference. Metallic complexes useful as radiopaque materials are also contemplated. The sheath 320 may be selectively made radiopaque in desired areas or made be fully radiopaque. Further, the distal portion 328 of the sheath 320 may have an inner core of tantalum, gold, platinum, iridium or combination of thereof and an outer member or layer of nitinol to provide a composite filament for improved radiocapicity or visibility. Alternatively, the sheath 320 may also have improved external imaging under magnetic resonance imaging (MRI) and/or ultrasonic visualization techniques. MRI is produced by complex interactions of magnetic and radio frequency fields. Materials for enhancing MRI visibility include, but are not limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the sheath marker 327 of the present invention may include ultrasound resonant material, such as but not limited to gold.

FIGS. 15a, 15b, 16 and 17 illustrate further alternative embodiments for the grasping members 375, 385, 395 of the present invention. In particular, FIGS. 15a and 15b respectively show an open and closed position for a grasping member 375 that is formed by a loop 374 and locking hook 376. This grasping member 375 can be designed with locking hook 376 having an outward bias, but configured to stay closed once caught on the edge of loop 374. Alternatively, the upper hook 376 and lower loop 374 can be designed to be actuated similar to the upper and lower portions of grasping member 165 discussed above. In FIGS. 16 and 17 the grasping members 385, 395 respectively include a lower hook 384, 394 and upper flap 386, 396. The grasping member 385 has an end portion of its flap 386 disposed on top or outside the hook 384 and can preferably be used for capturing a portion of a stent with a forward or distal movement of the member 385. In contrast, grasping member 395 has its flap 396 terminating inside the hook 394 and is more likely used for a backward or proximal movement of the member 395 to capture a portion of a stent 20.

Figure 18:
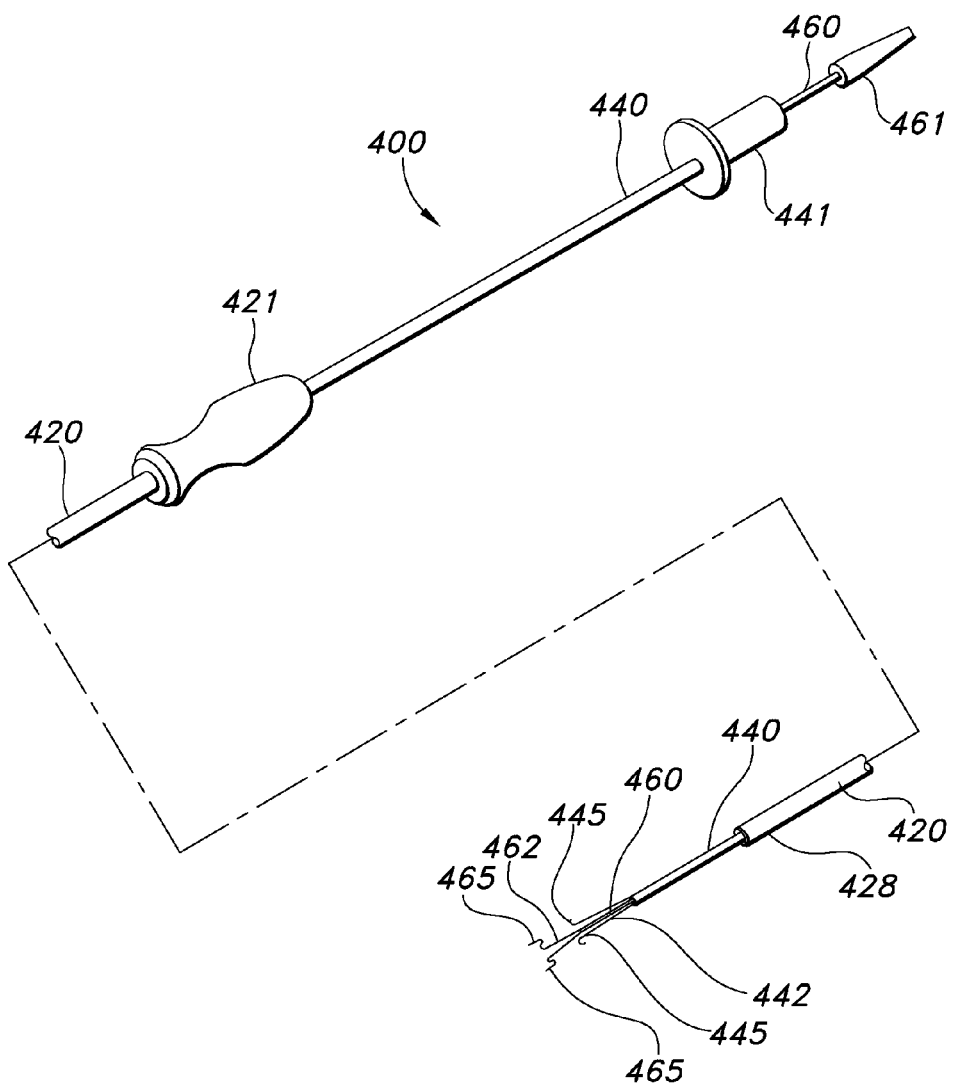
FIG. 18 illustrates a perspective view of a yet another alternative embodiment of the apparatus in accordance with the subject invention.

FIGS. 18-22 illustrate a further alternative embodiment of the apparatus of the present invention. In particular, FIG. 18 shows apparatus 400, which includes a sheath member 420, a contraction member 440 and a coupling member 460. The apparatus 400 in FIG. 18 is shown in an extended or deployed position. However, contraction member 440 and coupling member 460 can preferably be retracted so they are substantially disposed inside sheath 420. In this way as with the earlier embodiments, the retracted configuration of apparatus 400 can have a narrow profile and can be more easily navigated through the body. Once positioned in a desired location/configuration within a body lumen, contraction member 440 and coupling member 460 can be axially deployed from inside sheath 420.

The contraction member 440 and the coupling member 460 both coaxially extend through and are axially moveable with respect to an inner lumen of sheath 420. As with previous embodiments, the sheath 420, contraction member 440 and coupling member 460 each preferably include proximal handles 421, 441, 461 respectively for controlling the position and configuration of each member relative to the others. It should be understood that locking and/or retaining elements (not shown) can be included which can selectively and temporarily hold each handle 421, 441, 461 relative to the other(s).

The contraction member 440 is preferably formed as a sheath or rod with a lumen extending from end-to-end. Preferably, the proximal end of contraction member 440 includes a contraction handle 441 and the distal end includes axially extending strands or wires 442. A grasping member 445 is preferably formed at the distal end of each strand 442. It is preferred that the apparatus 400 include at least two contraction wires 442 in order to engage two circumferentially spaced portions of the targeted object. However, a greater or lesser number of wires 442 could be included. Also, similar to wires 362, the wires 442 are either secured or formed in such a way as to radially diverge from one another when unrestrained.

Figure 19:
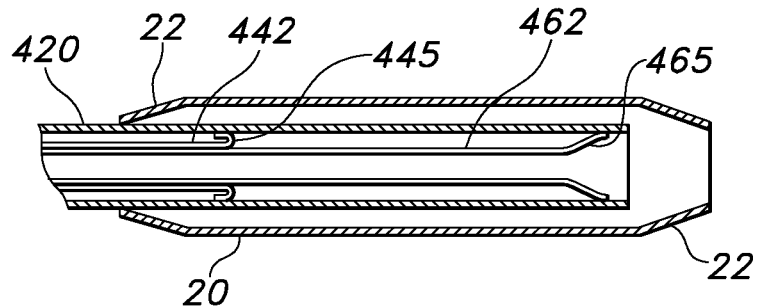
FIG. 19 illustrates a plan view of a distal portion of the apparatus of FIG. 18 in cross-section disposed within an intraluminal prosthesis.
Figure 20:
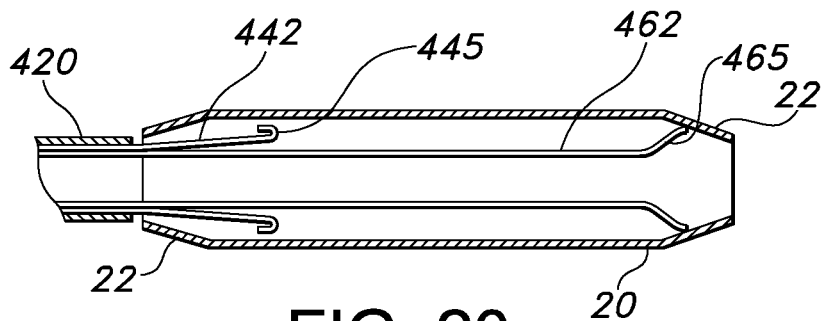
FIGS. 20-22 illustrate sequential plan views in cross-section of the apparatus of FIGS. 18 and 19 moving to capture and radially contract the intraluminal prosthesis.

The coupling member 460 is preferably similarly formed as a rod extending through and axially moveable with respect to the inner lumen of contraction member 440. While the greater length of coupling member 460 is preferably formed as a solid rod, it could be formed with a continuous inner lumen like the contraction member 400. Nonetheless, the coupling member 460 preferably includes a coupling handle 461 on the proximal end and strands or wires 462 axially extending from the distal end thereof. Preferably, the number of coupling wires 462 coincides with the number of contraction wires 442, however a fewer or greater number of wires 462 can be provided. Preferably, the number and configuration of contraction wires 442 and coupling wires 462 conforms to the number and configuration of the end loops or bends to be engaged on the target stent 20. Additionally, the coupling member 460 includes a grasping member 465 at the distal end of each wire 462. The wires, 442, 462 can be formed from the same or similar materials to those described above with respect to the wires 362 of apparatus 300 above. Also, similar to wires 362, 442, the wires 462 are either secured or formed in such a way as to radially diverge from one another when unrestrained. However, when in a retracted configuration, the sheath 420 radially constricts both wires 442, 462 and their respective grasping members 445, 465 as illustrated in FIG. 19. In this way, the elastic self-expanding wires 442, 462 deflect radially outwardly when the sheath 420 is pulled-back proximally, as illustrated in FIG. 20.

FIGS. 19-22 illustrate a sequence for using apparatus 400 to engage and radially contract stent 20. This embodiment is particularly suited for use on stents 20 designed to radially constrict when they are pulled or stretched longitudinally. The two sets of grasping members 445, 465 are preferably formed from one or more bends or hooks in the distal ends of the respective wires 442, 462. The contraction grasping member 445 and the coupling grasping member 465 are formed to engage and removeably capture respectively proximal and distal portions 22 of the stent 20. Thus, contraction grasping members 445 are preferably formed with an inner portion of its curve or hook facing proximally. In contrast, coupling grasping members 465 are formed with an inner curve facing generally distally, as shown.

As with the previous embodiments, the apparatus 400 is transluminally advanced in a retracted position to a site in a body lumen where the stent 20 has been deployed. In contrast to the previous embodiments, the distal portion of the entire retracted apparatus 400, including the sheath 420, is preferably advanced to a point where it is axially surrounded by the stent 20 before the sheath 420 is retracted. This initial position should have both sets of grasping members 445, 465 also located inside the stent 20, as illustrated by FIG. 19.

Next, the sheath 420 can be retracted by pulling the handle 421 proximally, while holding the other handles 441, 461 relatively still. By pulling back the sheath 420, the unrestrained contraction wires 442 and control wires 462 radially deflect and diverge bringing the grasping members 445, 465 in close proximity to the stent 20, as illustrated by FIG. 20.

Figure 21:
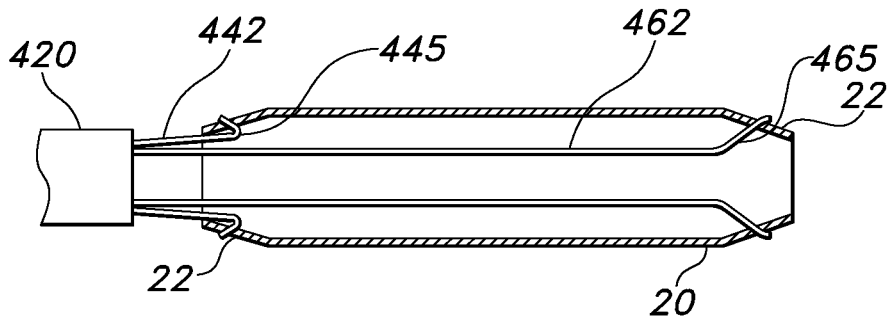

Thereafter, the operator can bring the sets of grasping members 445, 465 into engagement with the end portions 22 of the stent 20, as illustrated by FIG. 21. While both sets 445, 465 can be brought into engagement simultaneously, it may be easier for the operator to engage one set at a time. Thus, by delicately proximally pulling the contraction handle 441, while holding the coupling handle 461 relatively still the operator can engage one or more contraction grasping members 445 with the proximal stent end portion 22. Similarly, by delicately distally pushing the control handle 461, while holding the contraction handle 441 relatively still the operator can engage one or more control grasping members 465 with the distal stent end portion 22.

Figure 22:
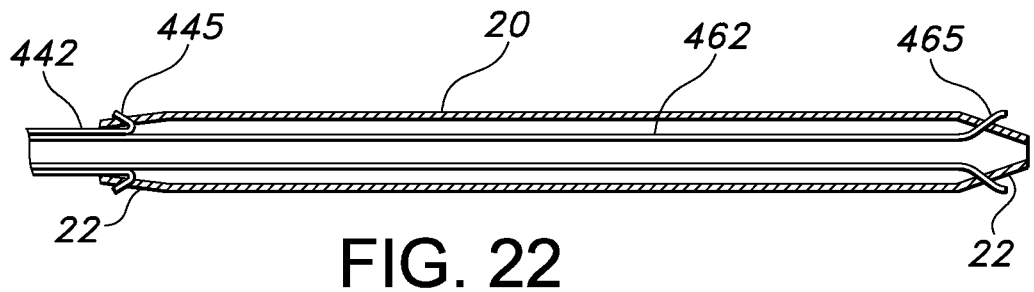

Once the grasping members 445, 465 are appropriately engaged with the stent 20, the operator moves handles 441, 461 relative to one another in order to further separate the proximal and distal grasping members 445, 465. This further separation pulls and stretches the stent 20, as illustrated in FIG. 22. The apparatus 400 takes advantage of the fact that longitudinal stretching of many stents 20, such as self-expanding stents, will generally cause them to radially constrict or reducing their overall outer diameter. Also, reducing the other diameter of the stent 20 tends to separate it from the surrounding tissue from which it may have been imbedded. Further, as the stent 20 constricts it will in turn radially constrict the position of the grasping members 445, 465 and the corresponding distal segments of the contraction and control wires 442, 462. Thus, the outer diameter of the stent 20 and the distal portions of the apparatus 400 are now configured in a narrow profile that can be more easily moved within a body lumen. Such movement can be distal, proximal and/or axially rotational movement. Additionally, the narrow profile is preferably such that the entire stent 20 or portions thereof can be easily pulled inside the sheath 420. Once inside the sheath, the stent 20 can then be moved and redeployed or removed entirely.

It should be understood that many of the elements from the various embodiments described above are interchangeable. For example, the grasping members 165 of apparatus 100 can be formed more like the grasping member 265, 365, 375, 385, 395, 465 of the other embodiments. Also, all the grasping members in any one embodiment do not need to be the same.

While various embodiments of the present invention are specifically illustrated and/or described herein, it will be appreciated that modifications and variations of the present invention may be effected by those skilled in the art without departing from the spirit and intended scope of the invention.

What is claimed is:

1. An apparatus for moving an object disposed within a body lumen, the apparatus comprising:
   a handle;
   a first sheath member attached to said handle, a contraction member, and a coupling member all axially movable relative to one another, the first sheath member being disposed about the contraction member, the contraction member being disposed about at least a portion of the coupling member;
   the contraction member being movable relative to the first sheath member between (i) a retracted position wherein a distal portion of the contraction member is disposed within the first sheath member and (ii) a deployed position wherein the distal portion of the contraction member is disposed outside the first sheath member;
   the coupling member comprising a plurality of wires, each having a proximal end located proximal to said handle and a distal end configured to engage a radially collapsible stent, wherein the distal end deflects radially outward as the coupling member is moved distally relative to the contraction member.

2. The apparatus of claim 1 wherein a distal end portion of the first sheath member includes radiopaque material.

3. The apparatus of claim 1 wherein at least one of the elongate wires is made of a material selected from the group consisting of stainless steel, nitinol, ceramic and polymer based materials.

4. The apparatus of claim 1 wherein the coupling member comprises a hook, the hook being formed by bending a distal portion of at least one of the plurality of elongate wires back upon a proximal portion of the same elongate wire.

5. The apparatus of claim 4 wherein a distal end portion of a first elongate wire is adjacent to a distal end portion of the hook.

6. The apparatus of claim 4 wherein the coupling member comprises a loop formed at a distal end of at least one of the plurality of elongate wires.

7. The apparatus of claim 6 wherein the hook is constructed to engage the loop as the hook moves proximally relative to the loop.

8. The apparatus of claim 1 wherein said first sheath member, said contraction member, and said coupling member are concentrically configured.

9. An apparatus for moving an expandable medical device disposed within a body lumen, the apparatus comprising:
   a handle;
   a sheath member for insertion into the body lumen, the sheath member having an inner radius defining a sheath lumen, the sheath member attached to said handle;
   a contraction member comprising a first wire having a proximal end located proximal to said handle, said first wire extending through the sheath lumen and being movable relative to the sheath member between (i) a retracted position wherein a distal end portion of the first wire is disposed within the sheath member and (ii) a capture position wherein the distal end portion of the first wire is disposed outside the sheath member, the first wire including a first hook at the distal end portion of the first wire, the first hook formed by bending the distal end portion of the first wire so that an inner portion of the first hook faces proximally, the distal end portion of the first wire deflecting radially outward as the contraction member is moved distally relative to the sheath member; and
   a coupling member comprising a second wire extending through the sheath lumen and being moveable relative to the sheath member between (i) a retracted position wherein a distal end portion of the second wire is disposed within the sheath member and (ii) a capture position wherein the distal end portion of the second wire is disposed outside the sheath member, the second wire including a second hook at the distal end portion of the second wire, the second hook formed by bending the distal end portion of the second wire so that an inner portion of the second hook faces distally, the distal end portion of the second wire deflecting radially outward as the coupling member is moved distally relative to the sheath member;
   whereby the first and second hooks are configured to cooperate to radially contract the expandable medical device as the coupling member is moved distally relative to the contraction member.

10. The apparatus of claim 9 wherein the first wire or the second wire is made of a material selected from the group consisting of stainless steel, nitinol, ceramic and polymer based materials.

11. The apparatus of claim 9 wherein the contraction member comprises a first plurality of elongate wires.

12. The apparatus of claim 11 wherein the coupling member comprises a second plurality of elongate wires.

13. An apparatus for moving an expandable medical device disposed within a body lumen, the apparatus comprising:
- a sheath member for insertion into the body lumen, the sheath member having an inner radius defining a sheath lumen;
- a contraction member comprising a first wire extending through the sheath lumen and being movable relative to the sheath member between (i) a retracted position wherein a distal end portion of the first wire is disposed within the sheath member and (ii) a capture position wherein the distal end portion of the first wire is disposed outside the sheath member, the first wire including a first hook at the distal end portion of the first wire, the first hook formed by bending the distal end portion of the first wire so that an inner portion of the first hook faces proximally, the distal end portion of the first wire deflecting radially outward as the contraction member is moved distally relative to the sheath member; and
- a coupling member comprising a second wire extending through the sheath lumen and being moveable relative to the sheath member between (i) a retracted position wherein a distal end portion of the second wire is disposed within the sheath member and (ii) a capture position wherein the distal end portion of the second wire is disposed outside the sheath member, the second wire including a second hook at the distal end portion of the second wire, the second hook formed by bending the distal end portion of the second wire so that an inner portion of the second hook faces distally, the distal end portion of the second wire deflecting radially outward as the coupling member is moved distally relative to the sheath member;
- whereby the first and second hooks are configured to cooperate to radially contract the expandable medical device as the coupling member is moved distally relative to the contraction member;
    - wherein the contraction member has more elongate wires than the coupling member.

* * * * *